United States Patent [19]
Noyori et al.

[11] Patent Number: 6,147,081
[45] Date of Patent: Nov. 14, 2000

[54] OPHTHALMIC SOLUTION

[75] Inventors: Sachiko Noyori; Noriko Takagi, both of Osaka, Japan

[73] Assignee: Rohto Pharmaceutical Co., Ltd., Osaka, Japan

[21] Appl. No.: 09/077,258

[22] PCT Filed: Sep. 26, 1997

[86] PCT No.: PCT/JP97/03444

§ 371 Date: Jan. 6, 1999

§ 102(e) Date: Jan. 6, 1999

[87] PCT Pub. No.: WO98/13040

PCT Pub. Date: Apr. 2, 1998

[30] Foreign Application Priority Data

Sep. 26, 1996 [JP] Japan ................................. 8/225198

[51] Int. Cl.$^7$ .................................................. A61K 31/435
[52] U.S. Cl. .......................... 514/277; 514/455; 514/912
[58] Field of Search .................................. 514/455, 277, 514/912

[56] References Cited

FOREIGN PATENT DOCUMENTS

| 0 670 161 A1 | 9/1995 | European Pat. Off. ...... A61K 31/125 |
| 61-246117 | 11/1986 | Japan ................................ A61K 9/08 |
| 2-311417 | 12/1990 | Japan ............................ A61K 31/68 |
| 7-118147 | 5/1995 | Japan . |
| 9-132526 | 5/1997 | Japan . |

OTHER PUBLICATIONS

M.H. Lessof et al., "Allergy," pp. 354–357 (1984).

James E.F. Reynolds et al., "Martindale," pp. 1145, 1534, 1804, 1898 (1993).

Research Disclosure, p. 914 (Dec., 1990).

Etsuko Takamura et al., "Igaku to Yakugaku" 34(3):507–513 (1995) with English Language descriptors attached).

Aramaki, T. and Taniguchi, Igaku To Yakugaku, 34(4):693–699, 1995.

Research Disclosure, p. 31997, 1990.

Rikagaku Jiten (Physicochemical Dictionary), 4th ed., p. 1288, 1989.

Hirokawa Yakukagakudaijiten (Pharmaceutical Dictionary), 2nd ed., p. 1396, 1990.

Fisher, "Comparison of budesonide and disodium cromoglycate for the treatment of seasonal allergic rhinitis in children," Annals of Allergy, 73(6):515–520, 1994.

English Translation of Rikagaku Jiten (Physiochemical Dictionary) (Reference AL in Supplemental IDS filed on Oct. 4, 1999).

Carpenter et al., "Chemical Burns of the Rabbit Cornea," Am. J. Ophthal. 29:1363–1372, 1949.

*Primary Examiner*—Zohreh Fay
*Attorney, Agent, or Firm*—Fish & Richardson P.C.

[57] ABSTRACT

A novel ophthalmic preparation containing menthol together with sodium cromoglycate and an antihistaminic is provided, which alleviates the unpleasant irritating eye-ache induced by sodium cromoglycate at the time of instillation and enhances the prompt antipruritic effect of the antihistaminic to strongly suppress itchiness of eyes immediately after instillation.

20 Claims, 1 Drawing Sheet

OPHTHALMIC SOLUTION

This is a 371 of International Patent Application No. PCT/JP97/03444, with an international filing date of Sep. 26, 1997, now pending.

TECHNICAL FIELD

This invention relates to an ophthalmic preparation comprising sodium cromoglycate, an antihistaminic, and menthol, which does not produce unpleasant irritating sensation on instillation and produces a prompt action and a strong antipruritic effect immediately after instillation.

BACKGROUND ART

Mechanisms of onset of typical allergy are known to include the following steps. First, antigens foreign to the organism invade organisms. When exposed to these antigens, the organisms produce IgE antibodies against the antigens. Produced IgE adheres to the surface of mast cells to form IgE-bound mast cells. On renewed invasion of the antigens to the organisms with IgE-bound mast cells, antigen-antibody reactions occur at the surface of IgE-bound mast cells. As a result, various chemical mediators, such as histamine or leucotrienes, are released through degranulation of the IgE-bound mast cells. Allergic reactions occur by the actions of these chemical mediators.

To suppress these allergic reactions various drugs have been developed. For example, sodium cromoglycate is an antiallergic agent that suppresses the degranulation of mast cells and the release of chemical mediators such as histamine. It is used clinically as inhalant, nasal drops, ophthalmic preparations, and drugs for internal use as a superb preventive antiallergic agent. Especially, in the ophthalmologic field, it is used as ophthalmic preparations for allergic conjunctivitis and vernal conjunctivitis in Japan. However, since the mechanism of action of sodium cromoglycate lies in the inhibition of degranulation of mast cells, it cannot block the effects of chemical mediators already released. It is inferior in prompt action and must be administered about 4 weeks ahead of the onset of symptoms. Another drawback of sodium cromoglycate ophthalmic preparations is that it may produce eye-ache (irritating pain) at the time of instillation (Allergy Immunological and Clinical Aspects, A Wiley Medical Publication and JP-A-Sho 61-246117). Thus, sodium cromoglycate ophthalmic preparations are not satisfactory from the viewpoint of eye irritation.

Consequently, in order to add an effect of prompt onset to antiallergic ophthalmic preparations containing sodium cromoglycate, combination ophthalmic preparations have been developed in which sodium cromoglycate is formulated together with an antihistaminic that blocks released histamine. For example, a combination ophthalmic preparation containing 1.0% of sodium cromoglycate and 0.015% of chlorpheniramine maleate, an antihistaminic, has been subjected to clinical test in Japan (Igaku to Yakugaku 34(3) 507, 1995). Combination ophthalmic preparations containing sodium cromoglycate and chlorpheniramine maleate, an antihistaminic, are being used abroad (MARTINDALE The Extra Pharmacopoeia 30th Edition, The Pharmaceutical Press, 1993). These combination ophthalmic preparations containing sodium cromoglycate and an antihistaminic can produce a prompt antipruritic effect due to the antihistaminic, even when applied after the onset of allergic symptoms. However, the antipruritic effect of these ophthalmic preparations are not so strong as to prevent patients from scratching eyes due to severe itchiness, which results in development of inflammation of eye mucosa. Furthermore, since alleviation of the eye-irritating action was not taken into consideration, patients had to endure the pain upon use.

JP-A-Sho 61-246117 discloses that it is desirable to dissolve sodium cromoglycate in a solvent containing sodium bicarbonate and boric acid and adjust pH to neutral in order to alleviate the eye-ache at the time of instillation of the antiallergic ophthalmic preparation. However, sodium cromoglycate ophthalmic preparations having preventive antiallergic effects with prompt onset of action could not be obtained by the method described in the above publication. Furthermore, a supplementary test conducted by the present inventors by actually prescribing the formula revealed that the eye-irritating action of the sodium cromoglycate ophthalmic preparation was not satisfactorily alleviated.

Aromatics, represented by menthol, are frequently formulated into ophthalmic preparations as a refrigerant. For example, it is disclosed in a literature (Research Disclosure 31997) that the drug compliance by patients is improved by addition of aromatics to a sodium cromoglycate preparation. EP-A-670161 discloses a pharmaceutical composition comprising 0.1–10% of sodium cromoglycate, 0.005–0.2% of bicyclic aromatic (camphor, eucalyptus oil, or mixtures thereof), and an aqueous base.

However, an ophthalmic preparation containing 3 elements of sodium cromoglycate, an antihistaminic, and menthol has not been developed yet.

DISCLOSURE OF THE INVENTION

An object of the present invention is to provide a sodium cromoglycate ophthalmic preparation which exhibits an antipruritic effect with prompt onset and alleviates eye-ache and unpleasant irritation.

Since it has been a problem that sodium cromoglycate ophthalmic preparations used so far were liable to produce eye-ache at the time of instillation, the present inventors intensively investigated in order to find out components that could alleviate the eye-ache at the time of instillation. As a result, the present inventors found that menthol, which has often been used for ophthalmic preparations as a refrigerant, could alleviate the irritating, unpleasant eye-ache occurring at the time of instillation of sodium cromoglycate.

Although the onset of action became prompt with the use of the conventional ophthalmic preparation containing sodium cromoglycate and an antihistaminic, an antipruritic effect of the ophthalmic preparation was not so strong as to immediately suppress the itching sensation of eyes. Thus, patients continued to scratch eyes because of severe itchiness, resulting in aggravation of ophthalmia of eye mucosa. The present inventors also paid attention to this problem and ardently studied on the components to be formulated into an ophthalmic preparation in order to obtain a strong antipruritic effect immediately after instillation. As a result, the present inventors found that menthol formulated into the ophthalmic preparation of the present invention could alleviate eye-ache and further improve the prompt antipruritic effect of the antihistaminic to thereby suppress severe itchiness of eyes immediately after instillation.

Furthermore, the present inventors found that menthol has an effect to habituate the patients to instillation through its refreshing sensation brought about to patients by fresh and cool nature and flavor, and its alleviation effect on eye-ache at the time of instillation. Thus, the present invention was completed.

The present invention relates to:
(1) An ophthalmic preparation comprising sodium cromoglycate, an antihistaminic, and menthol; and
(2) The ophthalmic preparation as described in (1) above in which the antihistaminic is chlorpheniramine maleate or diphenhydramine hydrochloride.

Menthol used in the present invention is described in a literature (The 13th Revision of Japanese Pharmacopoeia, D1050–1058). Commercially available one can also be used. Menthol of the present invention may be either l- or dl-form. Essential oils containing menthol like peppermint oil are also included in menthol of the present invention. The antihistaminic used for the present invention includes, for example, chlorpheniramine maleate, diphenhydramine hydrochloride, clemastine fumarate, and mequitazine. It is preferable to use chlorpheniramine maleate and diphenhydramine hydrochloride because their safety and effects are excellent. Chlorpheniramine maleate is superior in stability and is the most favorable antihistaminic.

Commercially available sodium cromoglycate can be used in the present invention. The content of sodium cromoglycate in the ophthalmic preparation is usually 0.5–5% (w/v). The content of the antihistaminic differs depending on the kind, but usually 0.005–0.1%, preferably 0.01–0.05%. The content of menthol is usually 0.001–0.1%, preferably 0.002–0.05%.

The pH of the ophthalmic preparation of the present invention is not particularly restricted as long as it is within the ophthalmologically acceptable range. It is usually adjusted to 4.0–7.0 with the ordinary method, but it is desirable to adjust it between 4.5 and 6.0. The osmotic pressure of the ophthalmic preparation of the present invention is usually adjusted to 0.5–5 pressure ratio with the ordinary method. It is desirable to adjust it to 0.8–2 pressure ratio.

As far as the problem of the present invention can be solved, the ophthalmic preparation of the present invention may further contain various additives such as buffering agents, isotonizing agents, solubilizers, preservatives, viscosity-increasing agents, chelating agents, and pH regulators.

Examples of the preservatives include chlorobutanol, sodium dehydroacetate, benzalkonium chloride, cetyl pyridinium chloride, phenethyl alcohol, parahydroxybenzoic acid esters, and benzethonium chloride. The buffers include, for example, borate buffers, phosphate buffers, carbonate buffers, and acetate buffers. The viscosity-increasing agents include, for example, methylcellulose, hydroxyethylcellulose, carboxymethylcellulose, hydroxypropyl- methylcellulose, polyvinyl alcohol, carboxymethylcellulose, chondroitin sulfate, and salts thereof. The solubilizers include, for example, polyoxyethylene hydrogenated castor oil, polyethylene glycol, polysorbate 80, and polyoxyethylene monostearate. The chelating agents include, for example, sodium edetate and citric acid. The stabilizers include, for example, sodium edetate and sodium hydrogen sulfite. The pH regulators include, for example, sodium hydroxide, potassium hydroxide, sodium carbonate, citric acid, phosphoric acid, acetic acid, and hydrochloric acid.

The usage and dose of the ophthalmic preparation of the present invention depends on symptoms, age, and the like of patients, but usually 1–6 times a day and 1–2 droplets per dose.

BEST MODE FOR CARRYING OUT THE INVENTION

Figure 1:
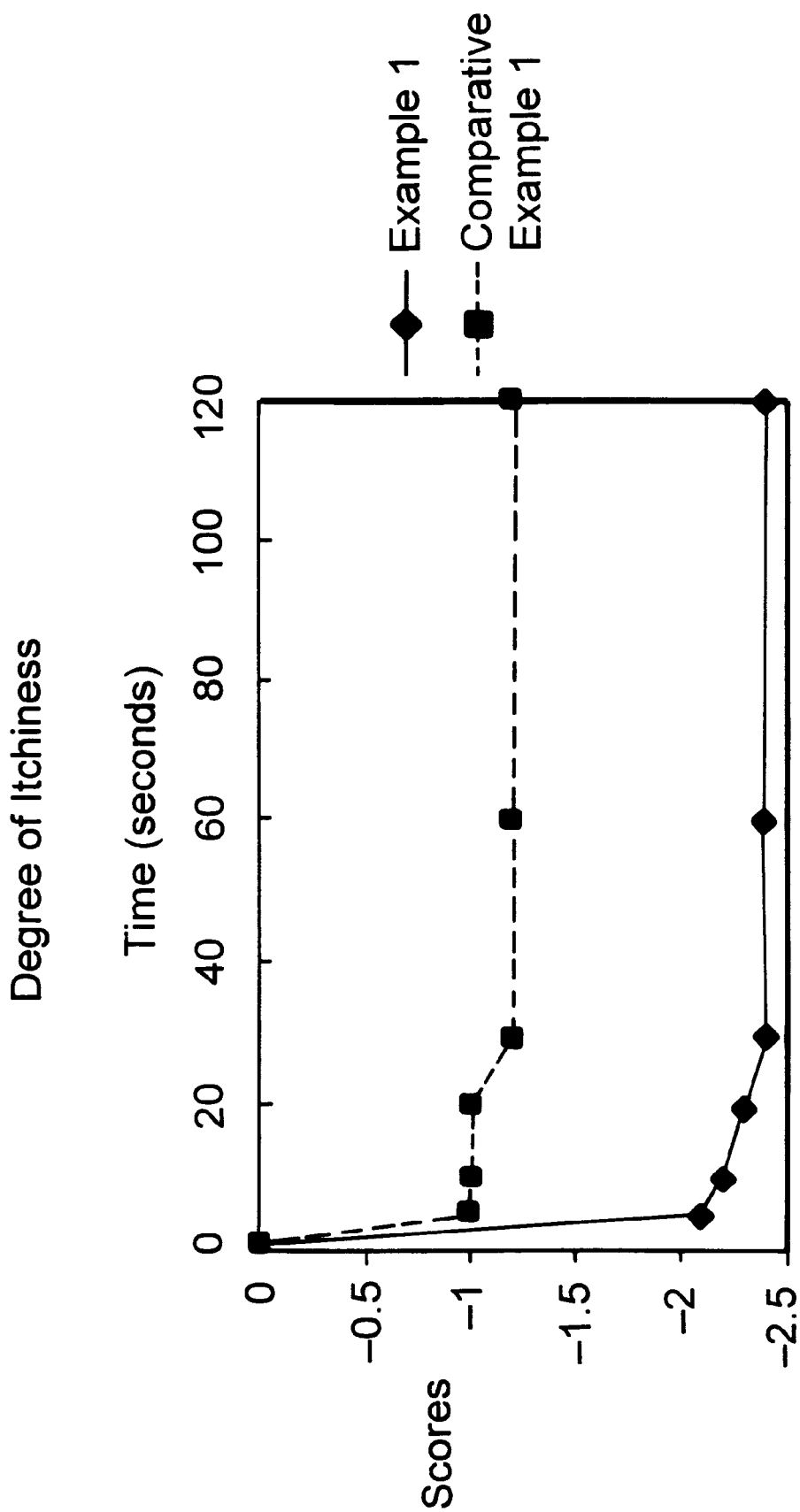
FIG. 1 shows the inhibitory effects of the ophthalmic preparation of the present invention on itchiness of eyes.

The present invention will be described below with reference to Examples, but is not to be construed to be restricted to these Examples.

EXAMPLE 1

Ophthalmic Preparation

| In 100 ml | |
| --- | --- |
| sodium cromoglycate | 1000 mg |
| chlorpheniramine maleate | 15 mg |
| l-menthol | 6 mg |
| benzalkonium chloride | 2 mg |
| borax | 10 mg |
| boric acid | 1800 mg |
| sterile distilled water | appropriate amount |
| Total volume | 100 ml |

The total volume is made to 100 ml by adding sterile distilled water and an ophthalmic preparation is obtained by the ordinary methods.

EXAMPLE 2

Ophthalmic Preparation

| In 100 ml | |
| --- | --- |
| sodium cromoglycate | 1000 mg |
| diphenhydramine hydrochloride | 20 mg |
| l-menthol | 6 mg |
| benzalkonium chloride | 2 mg |
| borax | 10 mg |
| boric acid | 1800 mg |
| sterile distilled water | appropriate amount |
| Total volume | 100 ml |

The total amount is made to 100 ml by adding sterile distilled water and an ophthalmic preparation is obtained by the ordinary methods.

Test Example

Effects of menthol contained in the ophthalmic preparation

The ophthalmic preparation of Example 1 and the ophthalmic preparation of Example 1 without l-menthol were prepared. Ten male and female adults with anamnesis of allergy were selected as subjects. Upon appearance of the allergic symptoms (itchiness) of eyes, the ophthalmic preparation without l-menthol was applied to left eyes and the ophthalmic preparation with l-menthol to right eyes, each 1–2 droplets. The degree of itchiness was self-evaluated before application (after 0 second) and at the predetermined period after application. Changes from the score of itchiness before application were determined in the course of time. FIG. 1 shows the mean values of "the score of itchiness at each time point minus that before application" of 10 subjects. Criteria for evaluation of itchiness are shown in Table 1. Irritating sensation on eyes at the time of instillation were also compared between the two preparations.

TABLE 1

"Criteria for evaluation of itchiness"

| Score | Strength of itchiness |
|---|---|
| 0 | not itchy |
| 1 | somewhat itchy |
| 2 | itchy |
| 3 | very itchy |

From these results, it was confirmed that the preparation of the present invention containing l-menthol could strongly suppress itchiness of eyes immediately after instillation as compared with the control (FIG. 1). As to irritating sensation on the eye, it was determined that 8 out of 10 subjects had upleasant eye-ache after instillation of the control preparation, while the preparation of the present invention did not produce eye-ache.

Similar experiments were performed using 20 mg of diphenhydramine as an antihistaminic instead of 15 mg of chlorpheniramine maleate were obtained.

INDUSTRIAL APPLICABILITY

The present invention provides the ophthalmic preparation containing sodium cromoglycate, an antihistaminic, and menthol. Using the ophthalmic preparation of the present invention, it is possible to suppress the severe itchiness of eyes immediately after instillation by virtue of enhanced antipruritic effects, thereby preventing aggravation of ophthalmia of eye mucosa resulted from scratching by patients. It is also possible to reduce the unpleasant irritating eye-ache given by the sodium cromoglycate ophthalmic preparation. Furthermore, fresh and cool nature of menthol improves the feeling of patients at the use of the preparation and promptly removes various unpleasant symptoms of eye allergy. These effects in combination with the alleviation of eye-ache at the time of instillation make it possible to habituate the patients to instillation.

What is claimed is:

1. An ophthalmic preparation comprising sodium cromoglycate, an antihistaminic, and menthol.

2. The ophthalmic preparation of claim 1, wherein said antihistaminic is chlorpheniramine maleate.

3. The ophthalmic preparation of claim 1, wherein said antihistaminic is diphenhydramine hydrochloride.

4. The ophthalmic preparation of claim 1, wherein said antihistaminic is selected from the group consisting of clemastine fumarate and mequitazine.

5. The ophthalmic preparation of claim 1, wherein the concentration of sodium cromoglycate is 0.5%–5% (weight to volume).

6. The ophthalmic preparation of claim 1, wherein the concentration of the antihistaminic is 0.005%–0.1% (weight to volume).

7. The ophthalmic preparation of claim 6, wherein the concentration of the antihistaminic is 0.01%–0.05% (weight to volume).

8. The ophthalmic preparation of claim 1, wherein said menthol is l-menthol.

9. The ophthalmic preparation of claim 1, wherein said menthol is dl-menthol.

10. The ophthalmic preparation of claim 1, wherein the concentration of menthol is 0.001%–0.1% (weight to volume).

11. The ophthalmic preparation of claim 10, wherein the concentration of menthol is 0.002%–0.05% (weight to volume).

12. The ophthalmic preparation of claim 1, wherein the pH is in the range of 4.0–7.0.

13. The ophthalmic preparation of claim 12, wherein the pH is in the range of 4.5–6.0.

14. The ophthalmic preparation of claim 1, further comprising one or more components selected from the group consisting of a buffering agent, an isotonizing agent, a solubilizer, a preservative, a viscosity-increasing agent, a chelating agent, a stabilizer, and a pH regulator.

15. A method of treating a subject with ophthalmic allergic symptoms, said method comprising applying the ophthalmic preparation of claim 1 to at least one eye of said subject.

16. The method of claim 15, wherein said subject is a human.

17. An ophthalmic preparation comprising sterile distilled water, 10 mg/ml sodium cromoglycate, 0.15 mg/ml chlorpheniramine maleate, and 0.06 mg/ml l-menthol.

18. The ophthalmic preparation of claim 17, further comprising benzalkonium chloride, borax, and boric acid.

19. An ophthalmic preparation comprising sterile distilled water, 10 mg/ml sodium cromoglycate, 0.2 mg/ml diphenhydramine hydrochloride, and 0.06 mg/ml l-menthol.

20. The ophthalmic preparation of claim 19, further comprising benzalkonium chloride, borax, and boric acid.

* * * * *

UNITED STATES PATENT AND TRADEMARK OFFICE
CERTIFICATE OF CORRECTION

PATENT NO. : 6,147,081
DATED : November 14, 2000
INVENTOR(S) : Sachiko Noyori and Noriko Takagi It is certified that error appears in the above-identified patent and that said Letters Patent is hereby corrected as shown below:

Column 5,
Line 16, change "upleasant" to -- unpleasant --.
Line 21, change "were obtained" to -- . Similar results as those obtained with chlorpheniramine maleate were obtained. --

Signed and Sealed this

Ninth Day of April, 2002

Attest:

Attesting Officer

JAMES E. ROGAN
Director of the United States Patent and Trademark Office